United States Patent [19]

Kummer et al.

[11] Patent Number: 4,533,757
[45] Date of Patent: Aug. 6, 1985

[54] CONTINUOUS HYDROFORMYLATION OF OLEFINICALLY UNSATURATED COMPOUNDS

[75] Inventors: Rudolf Kummer, Frankenthal; Wolfgang Richter, Ludwigshafen; Kurt Schwirten, Frankenthal; Peter Stops, Altrip, all of Fed. Rep. of Germany

[73] Assignee: BASF Aktiengesellschaft, Ludwigshafen, Fed. Rep. of Germany

[21] Appl. No.: 570,988

[22] Filed: Jan. 16, 1984

[30] Foreign Application Priority Data

Jan. 19, 1983 [DE] Fed. Rep. of Germany ....... 3301591

[51] Int. Cl.³ .............................................. C07C 45/50
[52] U.S. Cl. .................................... 568/454; 568/909
[58] Field of Search ................................ 568/454, 909

[56] References Cited

U.S. PATENT DOCUMENTS

| 3,904,547 | 9/1975 | Aycock et al. | 568/909 |
| 3,917,661 | 11/1975 | Pruett et al. | 568/454 |
| 4,060,557 | 11/1977 | Macaluso et al. | 568/454 |
| 4,151,209 | 4/1979 | Paul et al. | 568/454 |
| 4,247,486 | 1/1981 | Brewester et al. | 568/454 |
| 4,329,511 | 5/1982 | Hackman et al. | 568/909 |
| 4,374,278 | 2/1983 | Bryant et al. | 568/909 |

FOREIGN PATENT DOCUMENTS

| 1186455 | 2/1965 | Fed. Rep. of Germany | 568/454 |
| 1793069 | 2/1972 | Fed. Rep. of Germany | 568/454 |
| 2715685 | 10/1977 | Fed. Rep. of Germany | 568/454 |
| 988941 | 4/1965 | United Kingdom | 568/454 |
| 988943 | 4/1965 | United Kingdom | 568/454 |
| 1197847 | 7/1970 | United Kingdom | 568/454 |
| 2028677 | 3/1980 | United Kingdom | 568/909 |

Primary Examiner—Werren B. Lone
Attorney, Agent, or Firm—John H. Shurtleff

[57] ABSTRACT

Olefinically unsaturated compounds are continuously hydroformylated under from 2 to 30 bar and at from 80° to 130° C. using, as a catalyst, a rhodium complex which contains, as ligands, sparingly volatile compounds of the general formula I $$A\begin{matrix}\diagup R^1\\ -R^2\\ \diagdown R^3\end{matrix} \quad I$$

where A is phosphorus, arsenic, antimony or bismuth and $R^1$, $R^2$ and $R^3$ are each organic radicals, by a method in which the hydroformylation mixture consisting of liquid and gaseous components is removed from the reactor and is subjected to relatively high temperatures and/or relatively low pressures for a short time in a devolatilization column, the mixture at the same time being separated into a gas phase and a liquid phase, the gas phase is separated into the product and the recycle gas in a separator, and the recycle gas and the liquid phase from the devolatilization column are recycled to the reactor.

12 Claims, 1 Drawing Figure

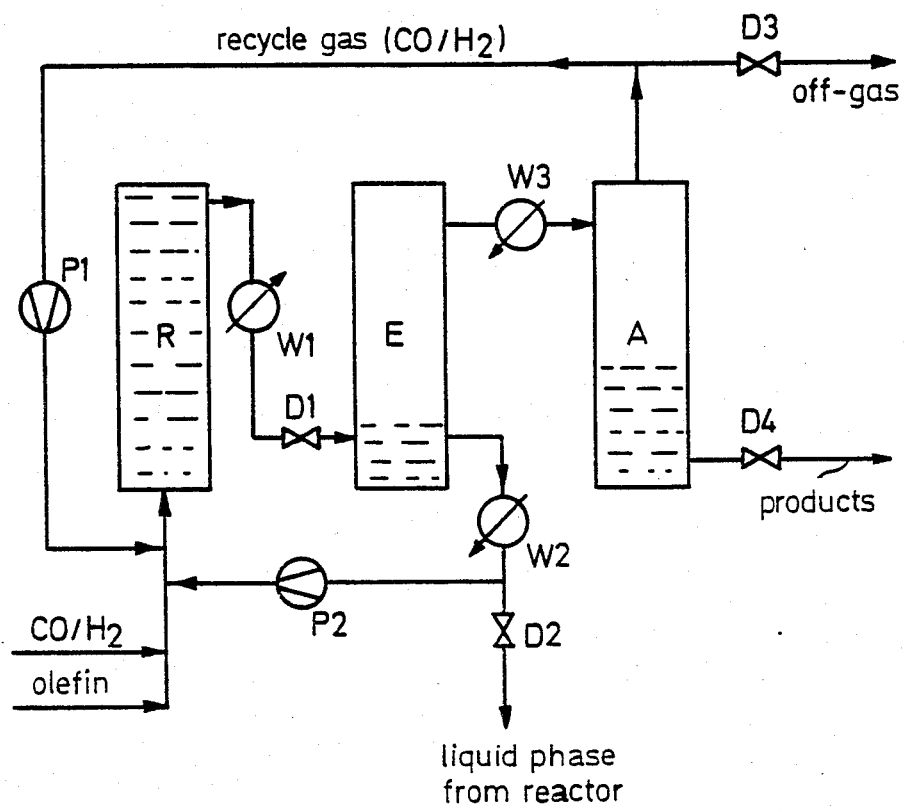

CONTINUOUS HYDROFORMYLATION OF OLEFINICALLY UNSATURATED COMPOUNDS

The present invention relates to an improved process for the continuous hydroformylation of olefinically unsaturated compounds under from 2 to 30 bar and at from 80° to 130° C. with the aid of, as a catalyst, a rhodium complex which contains, as ligands, sparingly volatile compounds of the general formula I

I where A is phospnorus, arsenic, antimony or bismuth and $R^1$, $R^2$ and $R^3$ are each organic radicals.

Apart from the improvement according to the invention, this process is well known, and is disclosed in, for example, DE-A-1 186 455 and DE-A-1 793 069.

Furthermore, it is well known that the products (mainly aldehydes but also the corresponding alcohols) can be obtained by either freeing the liquid reaction mixture from gaseous components and then working it up by distillation, or discharging the products in gaseous form, together with the gaseous reactants, from the hydroformylation reactor by the recycle gas method, isolating them from the gas stream and then recycling the major part of the gases to the reactor, as described in, for example, DE-A-2 715 685.

The first-mentioned method has the basic disadvantage that the catalyst present in the liquid reaction mixture is deactivated, if not damaged, under the distillation conditions, mainly owing to the absence of the $CO/H_2$ atmosphere in the presence of which the hydroformylation takes place.

The recycle gas method, in which the catalyst remains in the hydroformylation reactor, does not have the disadvantage described above; however, this method is only feasible where the products have a sufficiently high partial pressure to permit them to be discharged in sufficient amounts together with the recycled gas. If, however, the partial pressure were very low, disproportionately large amounts of gas would be required to discharge the products, with the result that the hydroformylation process would become uneconomical.

The possibility of making the recycle gas procedure more effective by increasing the hydroformylation temperature and hence the partial pressure of the products is not a reasonable one because it would lead to a shift from the optimum hydroformylation temperature and poorer results would be obtained: either undesirable hydrogenation of the olefin to a paraffin or of the aldehyde to an alcohol would take place, the isomerization of the olefins would increase at higher temperatures, or the proportion of linear aldehydes, which are generally preferred, would decrease.

It is an object of the present invention to provide a remedy for the stated disadvantages, and to recover the products for the hydroformylation mixtures in a more effective manner.

We have found that this object is achieved by an improved process for the continuous hydroformylation of olefinically unsaturated compounds under from 2 to 30 bar and at from 80° to 130° C. with the aid of, as a catalyst, a rhodium complex which contains, as ligands, sparingly volatile compounds of the general formula I

I where A is phosphorus, arsenic, antimony or bismuth and $R^1$, $R^2$ and $R^3$ are each organic radicals, wherein the hydroformylation mixture consisting of liquid and gaseous components is removed from the reactor and is subjected to relatively high temperatures and/or relatively low pressures for a short time in a devolatilization column, the mixture at the same time being separated into a gas phase and a liquid phase, the gas phase is separated into the product and the recycle gas in a separator, and the recycle gas and the liquid phase from the devolatilization column are recycled to the reactor.

The process is illustrated with reference to the drawing in which the single FIGURE is a schematic flow sheet of one embodiment of the invention. This process may be described as follows:

the partially liquid and partially gaseous reaction mixture which leaves the hydroformylation reactor R is advantageously brought, in a heat exchanger W1, to the higher temperature at which the devolatilization column E is operated in accordance with the invention.

The devolatilization in E can be carried out under the same pressure as in R, but it is advisable to reduce the pressure via a flow-control valve D1.

Separation of the reaction mixture into a gas phase and a liquid phase takes place in E. The residence time of about 2–10 minutes required for this is very much shorter than the residence time required in R for the hydroformylation, the latter time being about 4–8 hours; hence, in spite of the higher temperature, virtually no undesirable side reactions and secondary reactions are observed, although the reaction mixture is still under hydroformylation conditions here.

The liquid phase which leaves the devolatilization column can, if required, be cooled in the heat exchanger W2. In this case, it is advantageous from the point of view of heat technology if W1 and W2, and possibly W3 as well, are combined to form a common unit (not shown in the drawing).

The temperature in the devolatilization column E should as a rule be no less than 5° C. higher than the hydroformylation temperature. In practice, however, this temperature difference is generally from 10° to 50° C.

With regard to the discharge of the products from the devolatilization column E in gaseous form, the pressure is also important and can be the same as, or even lower than, the hydroformylation pressure since, for a lower total pressure corresponding to the partial pressure determined by the temperature, the volume of the hydroformylation products in the gas stream increases. Hence, it is advisable in general also to reduce the pressure when the temperature is increased. This pressure difference is preferably from 2 to 20 bar, with, of course, the proviso that it cannot be greater than $(p-1)$ where p is the hydroformylation pressure.

Since the partial pressure equilibria in E are established very rapidly, residence times here need be only from 1 to 30, as a rule from 2 to 10, minutes.

Since the liquid phase from R becomes enriched with high-boiling products in the course of time, it is necessary from time to time to separate off some of this liquid phase via the flow-control valve D2. The same applies with regard to the removal of the waste gas via D3. Both measures and apparatuses are, however, not features of the invention, and have therefore been mentioned only for the sake of completeness.

The liquid phase together with fresh synthesis gas ($CO/H_2$), fresh olefin and the recycle gas is passed once again into the reactor via the pump P2, which compensates both the unavoidable and the intentional pressure losses.

The gas phase from E is cooled in a conventional manner in the separator A or, advantageously, in an upstream heat exchanger W3 to such an extent that the products, mainly the aldehydes but also the alcohols and unreacted olefin and any paraffin formed, separate out in liquid form; these products are then removed from the system via pressure-release valve D4, and are treated further in a conventional manner. After a waste gas bleed stream has been separated off via D3, the gas phase, ie. the recycle gas which consists mainly of CO, $H_2$ and $N_2$, with or without small amounts of olefin and small amounts of the corresponding paraffin, is likewise recycled in a conventional manner to the hydroformylation reactor via the compressor P1.

The novel process hence embodies a reasonable decoupling of the conditions for optimum hydroformylation and an optimum discharge of gaseous product by the recycle gas method. Otherwise, within the general hydroformylation conditions according to the invention, the process is independent of the type of hydroformylation, so that a few basic explanations are sufficient here.

Suitable olefinically unsaturated compounds (which are sometimes abbreviated to olefins here) are mainly α-olefins of not more than 12 carbon atoms, but, for example, other α-olefinically unsaturated compounds, such as allyl alcohol, allyl acetate, acrylates, styrene and acrolein acetals, can also be used.

Olefinically unsaturated compounds having nonterminal double bonds undergo hydroformylation under the stated reaction conditions as a rule only to a small extent, if at all. However, for exceptional cases, the novel process would of course be just as suitable.

Although the lower olefins, eg. ethylene, propylene and but-1-ene, can also be more effectively hydroformylated using the novel process, the latter is more important in the case of α-olefins of 5 to 12 carbon atoms, since the partial pressure of the resulting aldehydes at the hydroformylation temperature is so low that the recycle gas will have to be circulated a disproportionately large number of times, ie. with substantial energy consumption.

A characteristic feature of the rhodium-catalyzed hydroformylation is the presence of the complex-forming ligands I, which are employed as a rule in a 3-fold to 500-fold molar excess, based on the rhodium. In general, the processes are not carried out using a ready-prepared Rh complex of this type, since the latter forms in situ from an Rh salt, eg. the acetate, and the ligands I under the hydroformylation conditions. Among the large number of ligands disclosed (cf. for example the literature cited at the outset), virtually only the phosphorus compounds, such as trialkyl phosphines, triaryl phosphines, trialkyl phosphites and triaryl phosphites, are of commercial importance, and among these ligands in turn triphenyl phosphine is preferred. In a particular case, the choice of ligand depends on the specific hydroformylation tasks, but these are not critical with regard to the present invention.

For practical reasons, care should be taken to ensure that the ligands I have sufficiently low volatility that they pass in no more than traces into the gas phase of the devolatilization column E, since otherwise they would contaminate the crude aldehyde and make it more difficult to work this up.

The rhodium concentration is in general in a conventional range, ie. about 50–500 ppm, based on the reaction mixture.

The molar ratio of CO to $H_2$ can be from about 10:90 to 90:10, depending on the object of the hydroformylation. In general, it is from 45:55 to 55:45, particularly where an aldehyde is desired as the product.

Compared with the prior art recycle gas method, the novel process permits the recovery of about 5–20 times the amount of products with the same amount of recycle gas. The amount of recycle gas, which in the conventional process is as a rule from 100 to 200 times the amount of fresh gas, can of course also be reduced correspondingly. In the novel process, the amount of recycle gas is advantageously about 10–30 times the amount of fresh gas.

The process according to the invention is particularly important for the preparation of $C_6$–$C_{13}$-alkanals from the corresponding α-olefins. These aldehydes are mainly reduced to the corresponding alcohols, which are used as components of ester-type plasticizers for plastics. Furthermore, they are oxidized to the corresponding carboxylic acids, which are important industrially as components of lubricants.

EXAMPLE

Hydroformylation of oct-1-ene

An experimental hydroformylation reactor R having a capacity of 40 liters was charged with 2.2 kg/hour of oct-1-ene, 0.94 $m^3$ (S.T.P.)/hour of a mixture of CO and $H_2$ in a volume ratio of 48:52, 24 $m^3$ (S.T.P.)/hour of a recycle gas, essentially consisting of 80 vol % of $H_2$, 15 vol % of CO and 5 vol % of $N_2$, and 4.0 kg/hour of recycled liquid.

The volume ratio of recycle gas to fresh gas was hence about 26:1.

The hydroformylation temperature was 105° C. and the pressure was 14 bar.

The concentration of the catalyst components was 100 ppm of rhodium (used in the form of Rh acetate) and 4.7% by weight of triphenyl phosphine (molar ratio of Rh to phosphine = 1:185).

The reaction mixture leaving the reactor, and containing about 6.7 kg of liquid constituents in addition to the recycle gas, was heated to 120° C. in heat exchanger W1, let down to 3 bar, and introduced into the devolatilization column E, and the recycle gas became laden with the products.

The catalyst-containing liquid phase E was cooled in the heat exchanger W2 and then recycled to the reactor via the pump P2.

The recycle gas was cooled to 20° C. under constant pressure (3 bar) by means of the heat exchanger W3, and was then separated, in the separator A, into a product-containing liquid phase and the recycle gas phase, which was returned to the reactor via the compressor P1.

2.71 kg/hour of crude product was obtained via the pressure-release valve D4, this product essentially having the following composition:

| | |
|---|---|
| n-nonanal | 2.16 kg |
| isononanal | 0.24 kg |
| nonanols | 0.03 kg |
| octenes | 0.25 kg |
| octane | 0.03 kg |
| | 2.71 kg |

The yield of the desired product n-nonanal was hence 77%, based on the octene employed, and the n-nonanal-/isononanal ratio was 9:1.

The olefin conversion, which serves as a measure of the catalyst reactivity, was 89% initially, 88% after an operating time of 1 week, 86% after 3 weeks and 85% after 6 weeks.

COMPARATIVE EXAMPLE 1

Conventional recycle gas method at the same hydroformylation temperature.

The hydroformylation of the octene was carried out in the same manner as in the process example, except that only the gas phase, ie. the recycle gas, was taken off from R; from this gas, the crude product was separated off in liquid form in the separator A.

The results essentially correspond to those of the process example, except that 210 m$^3$ (S.T.P.)/hour of recycle gas were required to discharge the product in gaseous form, ie. the recycle gas/fresh gas ratio was 223:1 in this case.

This uneconomical situation resulted in a consumption of about 30% more energy compared with the process example.

COMPARATIVE EXAMPLE 2

Conventional recycle gas method at a higher hydroformylation temperature

In contrast to the process example, the hydroformylation of the octene was carried out at a temperature at which the recycle gas/fresh gas ratio was about the same as in the process example. This temperature was about 170° C. The other conditions were the same as for the process example.

The recycle gas was fed directly to the separator A, and was freed there from the liquid components.

Although the recycle gas/fresh gas ratio and the total energy consumption were about the same as for the process example, the yield of n-nonanal deteriorated substantially, and was only 0.68 kg/hour (=25%). Moreover, 0.29 kg/hour of isononanal, 0.97 kg/hour of nonanols, 0.43 kg/hour of octenes and 0.23 kg/hour of octane were obtained as undesirable products.

Furthermore, as a result of the decreased catalyst activity, which in turn is caused by the higher thermal load, the conversion of the olefin to the hydroformylation products dropped from an initial value of 70% to 60% in the course of 7 days.

We claim:

1. In a process for the manufacture of aldehydes and alcohols by continuous hydroformylation of an olefinically unsaturated compound having up to 12 carbon atoms with carbon monoxide and hydrogen, said process being carried out in a hydroformylation reactor under a pressure from 2 to 30 bar and at a temperature from 80° to 130° C. in the presence of a rhodium complex catalyst which contains, as ligands, sparingly volatile compounds of the formula

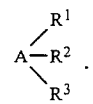

where A is phosphorus, arsenic, antimony or bismuth and $R^1$, $R^2$ and $R^3$ are each organic radicals and by subsequent separation of said aldehydes and alcohols from the hydroformylation reaction mixture, the improvement which comprises:

introducing the hydroformylation mixture as a crude reaction product consisting of both its liquid and gaseous components from the reactor into a devolatilization column;

devolatilizing said mixture in said column for a short time at a temperature which is higher and/or at a pressure which is lower than that prevailing in the hydroformylation reactor, and at the same time separating said reaction mixture in said column into a gas phase and a liquid phase;

cooling the gas phase from said column and conducting it to a separator to recover (a) a liquid product containing the produced aldehydes and alcohols and (b) a recycle gas; and recycling part of the gas from said separator to said reactor after removing a waste gas therefrom, and also recycling at least part of the liquid phase from the devolatilization column to said reactor.

2. A process as claimed in claim 1, which is carried out for the hydroformylation of an α-olefinically unsaturated compound.

3. A process as claimed in claim 2, which is carried out for the hydroformylation of a $C_5$–$C_{12}$-alk-1-ene.

4. A process as claimed in claim 1, wherein the devolatilization in the devolatilization column is carried out at a temperature which is from 10° to 50° C. higher than the hydroformylation temperature.

5. A process as claimed in claim 1, wherein the devolatilization in the devolatilization column is carried out at a lower pressure than the hydroformylation pressure.

6. A process as claimed in claim 1 wherein the temperature in the devolitization column is no less than 5° C. higher than the hydroformylation temperature.

7. A process as claimed in claim 1 wherein the residence time for the hydroformylation reaction is about 4 to 8 hours while the residence time for the devolitization is about 1 to 30 minutes.

8. A process as claimed in claim 1 wherein the residence tiem for the devolitization is about 2 to 10 minutes.

9. A process as claimed in claim 7 wherein the temperature in the devolitization column is about 10° to 50° C. higher than the hydroformylation temperature.

10. A process as claimed in claim 9 wherein the devolitization in said column is carried out at a lower pressure than the hydroformylation pressure.

11. A process as claimed in claim 10 wherein the olefinically unsaturated reactant is a $C_5$- to $C_{12}$-alk-1-ene.

12. A process as claimed in claim 1 wherein the olefinically unsaturated reactant is oct-1-ene.

* * * * *